US007674452B2

(12) United States Patent
Van et al.

(10) Patent No.: US 7,674,452 B2
(45) Date of Patent: *Mar. 9, 2010

(54) POLYMER COATING OF CELLS

(75) Inventors: Sang Van, San Diego, CA (US); Yasunobu Tanaka, San Diego, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 915 days.

This patent is subject to a terminal disclaimer.

(21) Appl. No.: 11/359,811

(22) Filed: Feb. 22, 2006

(65) Prior Publication Data

US 2006/0210530 A1 Sep. 21, 2006

Related U.S. Application Data

(60) Provisional application No. 60/662,612, filed on Mar. 16, 2005, provisional application No. 60/662,617, filed on Mar. 16, 2005.

(51) Int. Cl.
*A61Q 7/00* (2006.01)
(52) U.S. Cl. ............... 424/70.11; 424/78.27; 424/78.38
(58) Field of Classification Search ............. 424/70.11, 424/78.27, 78.38
See application file for complete search history.

(56) References Cited

U.S. PATENT DOCUMENTS

| 4,745,161 | A | 5/1988 | Saudek et al. |
|---|---|---|---|
| 5,374,681 | A | 12/1994 | Kroner et al. |
| 5,811,510 | A | 9/1998 | Papisov |
| 5,863,990 | A | 1/1999 | Papisov |
| 5,958,398 | A | 9/1999 | Papisov |
| 6,878,374 | B2 | 4/2005 | Yu et al. |
| 7,588,754 | B2 | 9/2009 | Van et al. |
| 2002/0031824 | A1 | 3/2002 | Greenberger |
| 2002/0082362 | A1 | 6/2002 | Brocchini et al. |
| 2002/0128177 | A1 | 9/2002 | Randal et al. |
| 2003/0113303 | A1 | 6/2003 | Schwartz |
| 2003/0120355 | A1 | 6/2003 | Hafeli et al. |
| 2003/0186916 | A1 | 10/2003 | Yu et al. |
| 2003/0215395 | A1 | 11/2003 | Yu et al. |
| 2004/0166089 | A1 | 8/2004 | Yu et al. |
| 2004/0258669 | A1 | 12/2004 | Dzau et al. |
| 2005/0037401 | A1 | 2/2005 | Cammack et al. |
| 2005/0049387 | A1 | 3/2005 | Van et al. |
| 2005/0080033 | A1 | 4/2005 | Van et al. |
| 2005/0089503 | A1 | 4/2005 | Sheng et al. |
| 2006/0210530 | A1 | 9/2006 | Van et al. |
| 2006/0258751 | A1 | 11/2006 | Zhao et al. |
| 2006/0263328 | A1 | 11/2006 | Van et al. |

FOREIGN PATENT DOCUMENTS

| EP | 0 683 177 | 11/1995 |
|---|---|---|
| WO | WO 9904824 | 2/1999 |
| WO | WO 2004009082 | 1/2004 |
| WO | WO 2005032597 | 4/2005 |

OTHER PUBLICATIONS

Abbattista, et al. "Stem Cells and Kidney Diseases," *Minerva Medica*, vol. 95, No. 5, pp. 411-418, 2004.
Garcia-Castro, et al. "Antitumoral Cell-Based Therapies," *Cancer Therapy*, vol. 1, pp. 163-171, 2003.
Hardikar, "Generating New Pancreas from Old," *Trends in Endocrinology and Metabolism*, vol. 15, No. 5, pp. 198-203, Jul. 2004.
Hildebrandt, et al. "Optical Imaging of Transferrin Targeted PEI/DNA Complexes in Living Subjects," *Gene Therapy*, vol. 10, pp. 758-764, 2003.
Smrekar, et al. "Tissue-Dependent Factors Affect Gene Delivery to Tumors in vivo," *Gene Therapy*, vol. 10, pp. 1079-1088, 2003.
Humes, et al. "Advances in Cell Therapy for Renal Failure" *Transplant Immunology*, vol. 12, pp. 219-227, 2004.
Kircheis, et al. "Tumor-Targeted Gene Delivery of Tumor Necrosis Factor-α Induces Tumor Necrosis and Tumor Regression Without Systemic Toxicity," *Cancer Gene Therapy*, vol. 9, pp. 673-680, 2002.
Melo, et al. "Molecular and Cell-Based Therapies for Protection, Rescue, and Repair of Ischemic Myocardium—Reasons for Cautious Optimism," *Circulation*, vol. 109. pp. 2386-2393, 2004.
Ogris, et al. "Tumor-Targeted Gene Therapy: Strategies for the Preparation of Ligand-Polyethylene Glycol-Polyethylenimine/DNA Complexes," *Journal of Controlled Release*, vol. 91, pp. 173-181, 2003.
Russell, et al. "Immunohistochemical Characterisation of the Monoclonal Antibody BLCA-38 for the Detection of Prostate Cancer," *Cancer Immunol Immunother*, vol. 53, pp. 995-1004, 2004.
Sato, et al. "Monoclonal Antibody to HER-2/NEU Receptor Enhances Radiosensitivity of Esophageal Cancer Cell Lines Expressing HER-2/NEU Oncoprotein," *Int. J. Radiation Oncology Biol. Phys*, vol. 61, No. 1, pp. 203-211, 2005.
Saxon, et al. "Chemical and Biological Strategies for Engineering Cell Surface Glycosylation," *Annu. Rev. Cell Dev. Biol.*, vol. 17, pp. 1-23, 2001.
International Preliminary Report on Patentability dated Sep. 18, 2007 for International Application No. PCT/US2006/006568.
International Search Report dated Jul. 11, 2006 and issued to a related international application.
Written Opinion issued to a related international application.
Hoppe, V. "Herstellung von Spiropolyamiden," Die Makromolekular Chemie 124: 274-277 (1969).
International Search Report and Written Opinion dated Jul. 26, 2006 for International Application No. PCT/US2006/012420.
Office Action dated Oct. 24, 2008 for U.S. Appl. No. 11/126,878, including a characterization of Hoppe, listed above as ref No. 2, by the Examiner.
Bourke, S.L. and Kohn, J. "Polymers derived from the amino acid L-tyrosine: polycarbonates, polyarylates and copolymers with poly(ethylene glycol)." *Adv. Drug Del. Rev.*, 2003, 55(4):447-466.
Heller, J.; Barr, J.; Ng, S.Y.; Abdellauoi, K.S. and Gurny, R. "Poly(ortho esters): synthesis, characterization, properties and uses." *Adv. Drug Del. Rev.* 2002, 54(7):1015-1039.
Kumar, N.; Lancer, R.S. and Domb, A.J. "Polyanhydrides: an overview." *Adv. Drug Del. Rev.* 2002, 54(7):889-910.

(Continued)

*Primary Examiner*—Michael G. Hartley
*Assistant Examiner*—James Rogers
(74) *Attorney, Agent, or Firm*—Knobbe Martens Olson & Bear LLP

(57) ABSTRACT

Polymers and methods of making them are described. The polymers may be used to coat living cells. The polymer-coated cells are useful in cell therapy applications.

11 Claims, 4 Drawing Sheets

OTHER PUBLICATIONS

Murthy, N., Thng, Y. X., Schuck, S., Xu, M. C. & Fréchet, J. M. J., "A Novel Strategy for Encapsulation and Release of Proteins: Hydrogels and Microgels with Acid-Labile Acetal Cross-Linkers." J. Am. Chem. Soc., 2002, 124(42):12398-12399.

Panyam J, Labhasetwar V. "Biodegradable nanoparticles for drug and gene delivery to cells and tissue." *Adv Drug Deliv Rev.* 2003, 55(3):329-47.

Tomlinson, R. et al., "Pendent Chain Functionalized Polyacetals That Display pH-Dependent Degradation: A Platform for the Development of Novel Polymer Therapeutics." Macromolecules, 2002, 35:473-480.

Tomlinson R, Heller J, Brocchini S, Duncan R. "Polyacetal-doxorubicin conjugates designed for pH-dependent degradation." Bioconjug Chem. Nov.-Dec. 2003;14(6):1096-106.

Uhrich, K.E.; Cannizzaro, S.M.; Lancer, R.S. and Shakeshelf, K.M. "Polymeric systems for controlled drug release." *Chem. Rev.* 1999, 99(11): 3181-3198.

International Preliminary Report on Patentability dated Nov. 13, 2007 for PCT Application No. PCT/US2006/012420 filed Apr. 3, 2006.

Polymer IA

POLYMER COATING OF CELLS

RELATED APPLICATIONS

This application claims priority to U.S. Provisional Application Nos. 60/662,612 and 60/662,617, both filed Mar. 16, 2005, both of which are hereby incorporated by reference in their entireties.

BACKGROUND OF THE INVENTION

1. Field of the Invention

This invention relates generally to coating and delivery of cells. The coating material includes biodegradable polymers containing hydrophobic groups, hydrophilic groups, and reporters. The polymer coated cells may be used in cell-based therapies.

2. Description of the Related Art

While therapeutic advances in the last decade have produced many effective drugs and treatments, such treatments usually are unable to completely correct or reverse disease states because most disease states are caused by complex interactions between cell components. Cell therapy holds much promise to not only provide relief from disease symptoms, but to actually reverse disease states. Blood transfusions and bone marrow transplants are examples of successful use of cell-based therapeutics There are currently no effective therapies for many acquired and congenital cardiovascular, pulmonary, and hematologic diseases and disorders. Recent discoveries in stem cell biology present new opportunities for the use of cell-based therapies in disease areas with critical, unmet medical needs. Adult, cord blood, embryonic and fetal stem cells hold great potential for use in new strategies aimed at the regeneration and repair of damaged or diseased cardiovascular, lung, and blood tissues.

SUMMARY OF THE INVENTION

Embodiments of the invention are directed to polymers which include at least one recurring unit represented by a formula selected from formulas (I), (II), and (III):

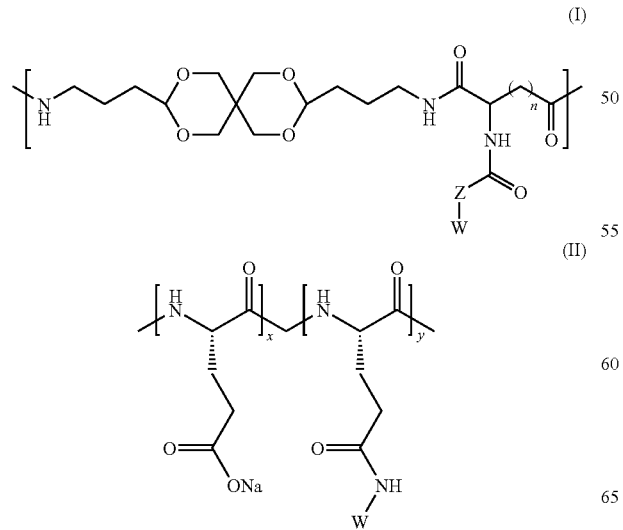

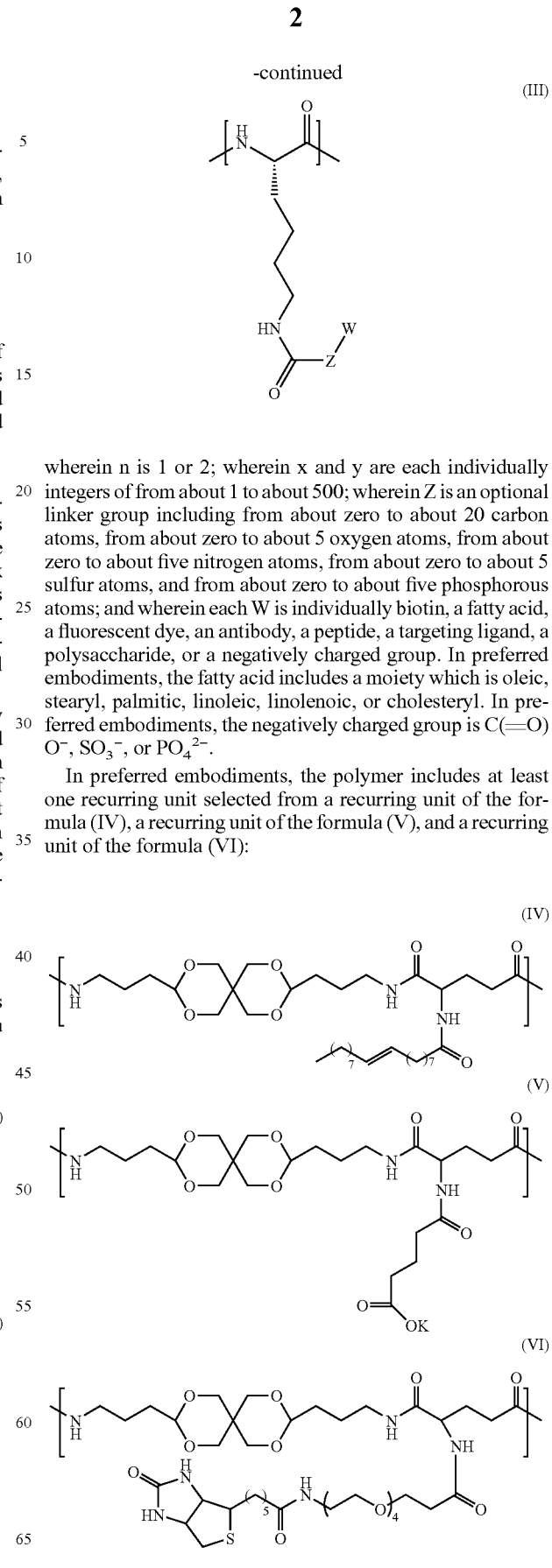

wherein n is 1 or 2; wherein x and y are each individually integers of from about 1 to about 500; wherein Z is an optional linker group including from about zero to about 20 carbon atoms, from about zero to about 5 oxygen atoms, from about zero to about five nitrogen atoms, from about zero to about 5 sulfur atoms, and from about zero to about five phosphorous atoms; and wherein each W is individually biotin, a fatty acid, a fluorescent dye, an antibody, a peptide, a targeting ligand, a polysaccharide, or a negatively charged group. In preferred embodiments, the fatty acid includes a moiety which is oleic, stearyl, palmitic, linoleic, linolenoic, or cholesteryl. In preferred embodiments, the negatively charged group is $C(=O)O^-$, $SO_3^-$, or $PO_4^{2-}$.

In preferred embodiments, the polymer includes at least one recurring unit selected from a recurring unit of the formula (IV), a recurring unit of the formula (V), and a recurring unit of the formula (VI):

In some preferred embodiments, the polymer includes a recurring unit of the formula (IV). In some preferred embodiments, the polymer includes a recurring unit of the formula (V). In some preferred embodiments, the polymer includes a recurring unit of the formula (VI). In some preferred embodiments, the polymer includes a recurring unit of the formula (IV), a recurring unit of the formula (V), and a recurring unit of the formula (VI).

Preferred embodiments are directed to a polymer which includes a recurring unit of the formula (VII):

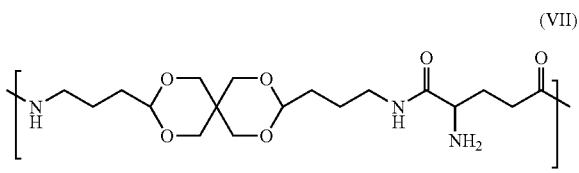

(VII)

In preferred embodiments, the polymer includes a recurring unit of the formula (VIII):

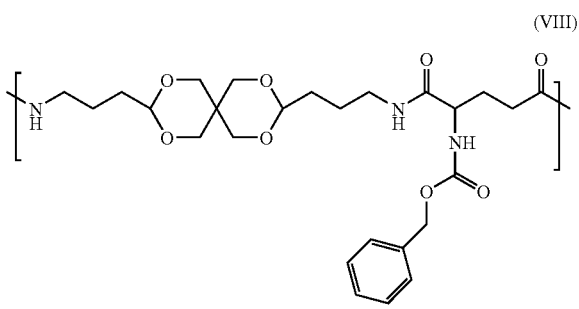

(VIII)

In preferred embodiments, the polymer includes a recurring unit of the formula (IX):

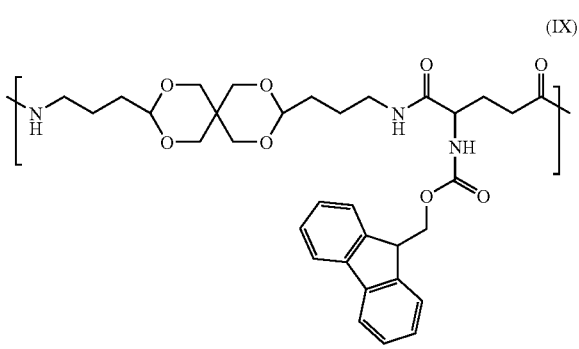

(IX)

Embodiments of the invention are directed to methods of making the polymers that include a recurring unit of the formula (I) as described above, which includes amidating a polymer comprising a recurring unit of the formula (VII) as described above with a reagent which is NHS-dPEG4-Biotin, NHS-dPEG4-peptide, glutaric anhydride, fatty acid chloride, or activated ester NHS.

Embodiments of the invention are directed to methods of making polymers which include recurring units of the formula (II) as described above, which include amidating a polymer that includes a recurring unit selected from a glutamic acid recurring unit and a glutamic acid salt recurring unit, with an amino-peptide and a fatty acid amine.

Embodiments of the invention are directed to methods of making polymers which include a recurring unit of the formula (III) as described above, which include amidating a polymer that includes a recurring unit selected from a lysine recurring unit and a lysine salt recurring unit, with a reagent which is NHS-dPEG4-Biotin, NHS-dPEG4-peptide, glutaric anhydride, fatty acid chloride, or activated ester NHS.

Embodiments of the invention are directed to methods of making polymers that include a recurring unit of the formula (IV) as described above, which includes amidating a polymer that includes a recurring unit of the formula (VII) as described above with oleic chloride.

Embodiments of the invention are directed to methods of making polymers that include a recurring unit of the formula (V) as described above, which include amidating a polymer that includes a recurring unit of the formula (VII) as described above with glutaric anhydride and potassium carbonate.

Embodiments of the invention are directed to methods of making polymers that include a recurring unit of the formula (VI) as described above, which include amidating a polymer that includes a recurring unit of the formula (VII) as described above with NHS-dPEG4-Biotin.

Embodiments of the invention are directed to methods of making polymers that include a recurring unit of the formula (VII) as described above, which include removing a protecting group from a polymer that includes a recurring unit of the formula (VIII) as described above via palladium/carbon catalytic hydrogenation.

Embodiments of the invention are directed to methods of making a polymer which includes a recurring unit of the formula (VII) as described above, which include treating a polymer that includes a recurring unit of the formula (IX) as described above with 20% piperidine.

Embodiments of the invention are directed to methods of making polymers which include a recurring unit of the formula (VIII) as described above, which include amidating a diamine and a glutamic amino acid derivative, wherein the diamine is represented by the formula:

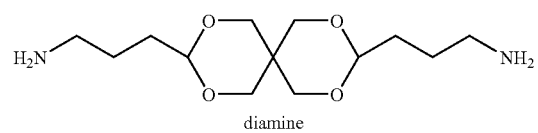

diamine and wherein the glutamic amino acid derivative is represented by the formula:

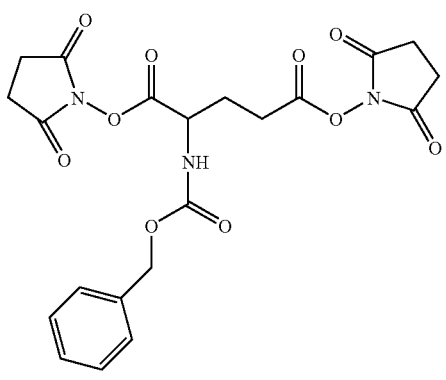

glutamic amino acid derivative

Embodiments of the invention are directed to methods of making polymers that include a recurring unit of the formula (IX) as described above, which include amidating a diamine and a glutamic amino acid derivative, wherein the diamine is represented by the formula:

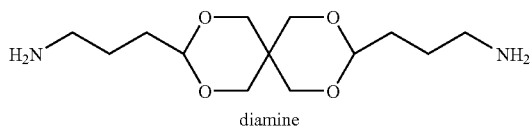
diamine and wherein the glutamic amino acid derivative is represented by the formula:

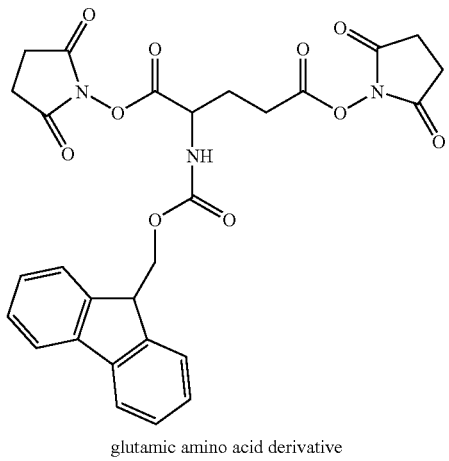
glutamic amino acid derivative

Embodiments of the invention are directed to a polymer-coated cell which includes a living cell and a polymer which includes at least one recurring unit represented by a formula selected from formulas (I), (II), and (III) as described above, where the polymer is non-covalently attached to at least a portion of the exterior of the living cell. Preferably, the living cell is an epithelial cell, an endothelial cell, a progenitor cell, a mature stem cell, or an embryonic stem cell.

In preferred polymer-coated cell embodiments, the polymer includes at least one recurring unit selected from a recurring unit of the formula (IV), a recurring unit of the formula (V), and a recurring unit of the formula (VI) as described above.

In preferred embodiments, W in formulas (I), (II), and (III) is a targeting ligand. More preferably, the targeting ligand is transferrin or epidermal growth factor. In some preferred embodiments, the antibody is to a receptor that is overexpressed in cancer cells. In preferred embodiments, the fatty acid includes a moiety which is oleic, stearyl, palmitic, linoleic, linolenoic, or cholesteryl. In preferred embodiments, the negatively charged group is $C(=O)O^-$, $SO_3^-$, or $PO_4^{2-}$.

In preferred polymer-coated cell embodiments, the living cell is a mammalian cell. More preferably, the living cell is a human cell.

Embodiments of the invention are directed to a method for coating a living cell, comprising intermixing the living cell with a polymer which includes at least one recurring unit represented by a formula selected from formulas (I), (II), and (III) as described above, wherein the polymer is intermixed with the living cell in an amount effective to at least partially coat the exterior of the living cell.

In preferred embodiments, the polymer includes at least one recurring unit selected from a recurring unit of the formula (IV), a recurring unit of the formula (V), and a recurring unit of the formula (VI), as described above.

In preferred polymer-coated cell embodiments, the living cell is an epithelial cell, an endothelial cell, a progenitor cell, a mature stem cell, or an embryonic stem cell. In preferred embodiments, the fatty acid includes a moiety which is oleic, stearyl, palmitic, linoleic, linolenoic, and cholesteryl. In preferred embodiments, the negatively charged group is $C(=O)O^-$, $SO_3^-$, or $PO_4^{2-}$.

In preferred embodiments, the living cell is a mammalian cell. More preferably, the living cell is a human cell.

Embodiments of the inventions are directed to a method of treating a disease or injury which comprises administering the polymer coated cell to an individual in need thereof. In preferred embodiment, the individual is a mammal. Preferably, the mammal is a human.

In preferred embodiments, the administration is by injection. Preferably, the administration is by injection into an organ which is diseased or injured or into a vascular system which feeds the diseased or injured organ. In some preferred embodiments, administration is into a tail vein of a mouse.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENTS

Figure 1:
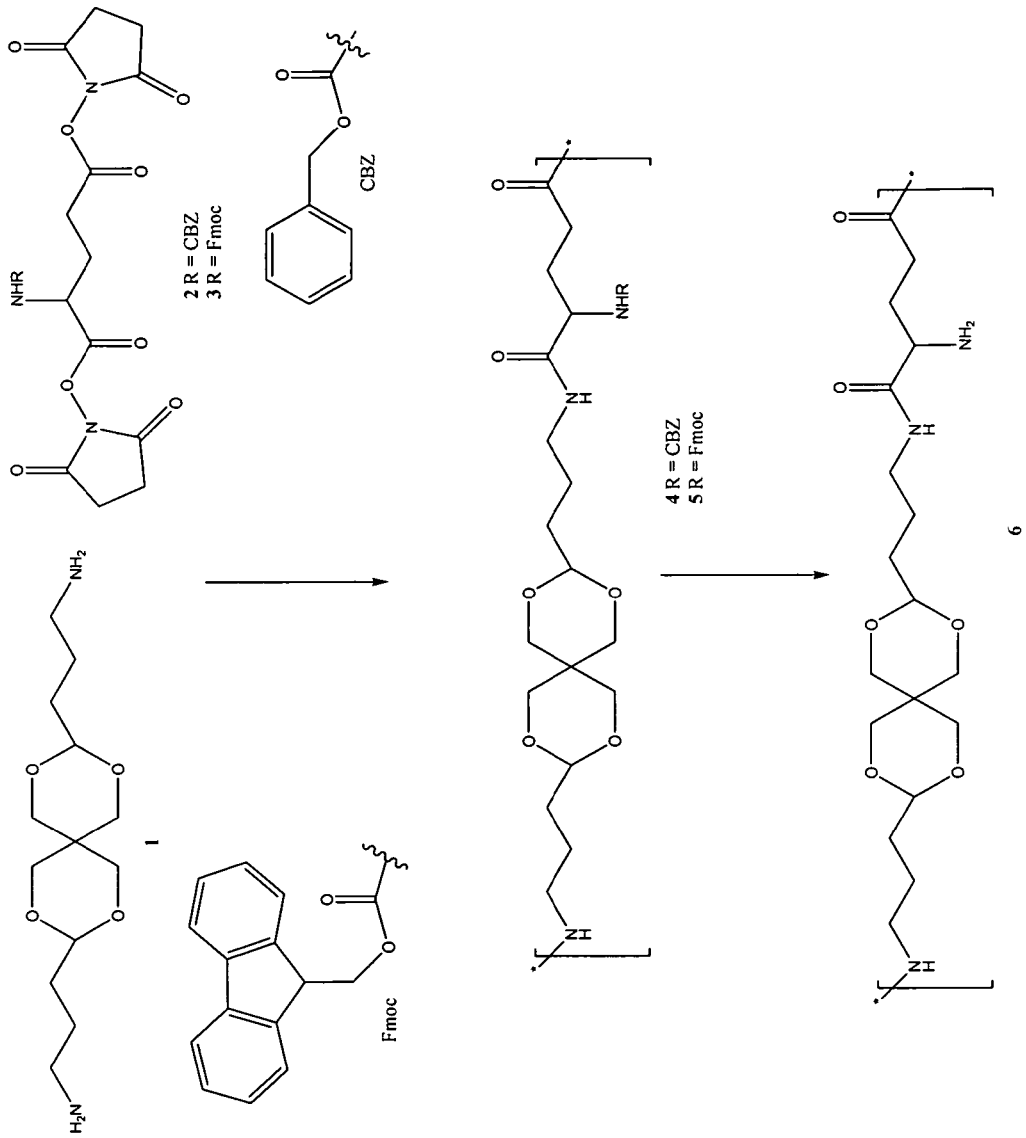
FIG. 1 shows a reaction scheme according to an embodiment for preparation of polymers by amidation of a diamine and a glutamic amino acid derivative.

These and other features of this invention will now be described with reference to the drawings of preferred embodiments which are intended to illustrate and not to limit the invention.

The invention relates generally to biodegradable polymer, methods for making them, and methods of using them for various applications, including cell delivery and transplantation, and particularly for transplantation of autologous and non-autologous progenitor cells or stem cells. In an embodiment, a method provides therapeutic effects for a wide range of diseases in which cell-based products have been reduced or lost due to disease or injury. These cell-based products may be replaced by cell implantation techniques.

The term "progenitor cells" is a broad term and refers to cells which are capable of development into a distinct cell types or lineages within a tissue or organ by a series of cell divisions.

The term "stem cell" is a broad term and refers to cells which are capable of regeneration into multiple cell types or lineages. The term "stem cell" includes both adult stem cells and embryonic stem cells.

Polymers and Methods for Making Them

An embodiment provides a polymer comprising at least one recurring unit represented by a formula selected from the group consisting of formulas (I), (II), and (III):

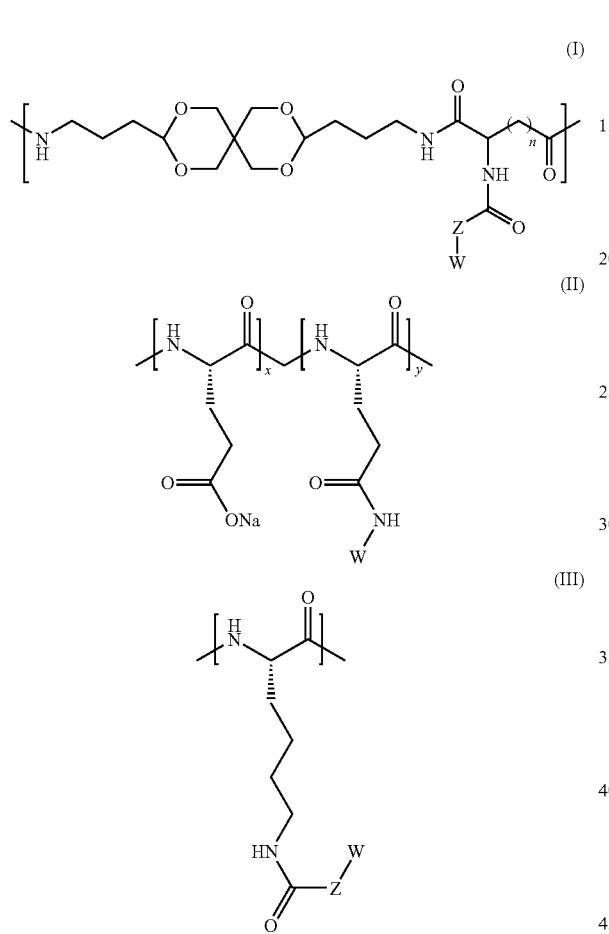

wherein n is 1 or 2; wherein x and y are each individually integers of from about 1 to about 500; wherein Z is an optional linker group comprising from about zero to about 20 carbon atoms, from about zero to about 5 oxygen atoms, from about zero to about five nitrogen atoms, from about zero to about 5 sulfur atoms, and from about zero to about five phosphorous atoms; and wherein each W is individually selected from the groups consisting of biotin, a fatty acid, a fluorescent dye, an antibody, a peptide, a targeting ligand, a polysaccharide, and a negatively charged group. In an embodiment, the fatty acid comprises a moiety selected from the group consisting of oleic, stearyl, palmitic, linoleic, linolenoic, and cholesteryl. In an embodiment, the negatively charged group is selected from the group consisting of $C(=O)O^-$, $SO_3^-$, or $PO_4^{2-}$.

Examples of polymers that comprise recurring units of the formula (I) include polymers that comprise recurring units of the formula (IV), polymers that comprise recurring units of the formula (V), and polymers that comprise recurring units of the formula (VI):

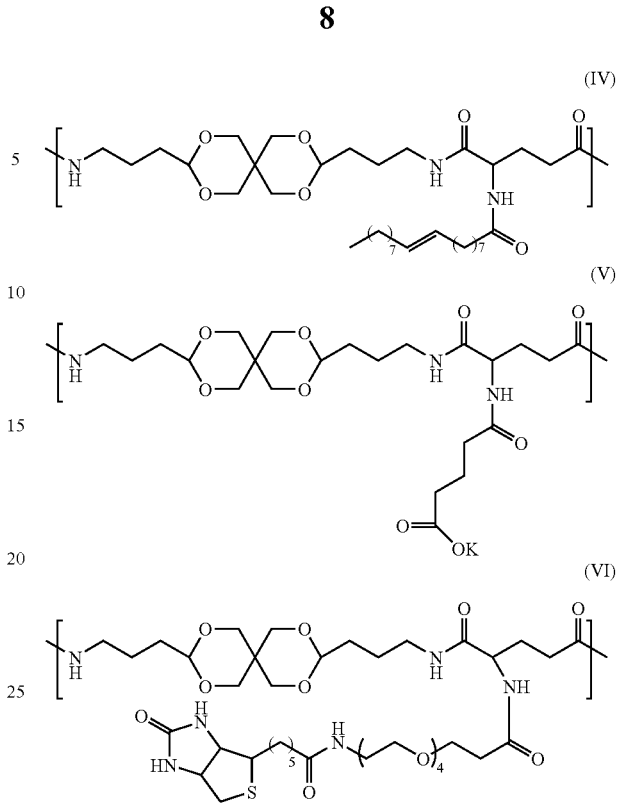

Thus, in an embodiment, a polymer that comprises a recurring unit of the formula (I) comprises at least one recurring unit selected from the group consisting of a recurring unit of the formula (IV), a recurring unit of the formula (V), and a recurring unit of the formula (VI). Polymers that comprise a recurring unit of the formula (I) may be copolymers. For example, in an embodiment, a polymer that comprises a recurring unit of the formula (I) comprises two or more recurring units selected from the group consisting of a recurring unit of the formula (IV), a recurring unit of the formula (V), and a recurring unit of the formula (VI). As another example, a polymer that comprises a recurring unit of the formula (I) comprises a recurring unit of the formula (IV), a recurring unit of the formula (V), and a recurring unit of the formula (VI).

Polymers that comprise a recurring unit of the formula (I) may be prepared in various ways. For example, an embodiment provides a polymer that comprises a recurring unit of the formula (VII):

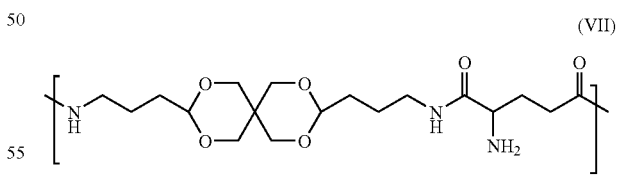

Polymers that comprise a recurring unit of the formula (I) may be prepared by a process that comprises amidating a polymer that comprises a recurring unit of the formula (VII) with a reagent selected from the group consisting of NHS-dPEG$_4$-Biotin, NHS-dPEG$_4$-peptide, glutaric anhydride, fatty acid chloride, and activated ester NHS. For example, in one embodiment, a method of making a polymer that comprises a recurring unit of the formula (IV) comprises amidating a polymer that comprises a recurring unit of the formula (VII) with oleic chloride. In another embodiment, a method of making a polymer that comprises a recurring unit of the formula (V) comprises amidating a polymer that comprises a recurring unit of the formula (VII) with glutaric anhydride and potassium carbonate. In yet another embodiment, a method of making a polymer that comprises a recurring unit of the formula (VI) comprises amidating a polymer that comprises a recurring unit of the formula (VII) with NHS-dPEG$_4$-Biotin. The working examples provided below describe specific reaction conditions for carrying out an exemplary amidation reaction. Routine experimentation may be used to identify appropriate amidation conditions to prepare other polymers that comprise a recurring unit of the formula (I).

Polymers that comprise a recurring unit of the formula (II) may be prepared by a process that comprises amidating a polymer that comprises a recurring unit selected from the group consisting of glutamic acid recurring unit and glutamic acid salt recurring unit, with an amino-peptide and a fatty acid amine. Polymers that comprise a recurring unit of the formula (III) may be prepared by a process that comprises amidating a polymer that comprises a recurring unit selected from the group consisting of lysine recurring unit and lysine salt recurring unit, with a reagent selected from the group consisting of NHS-dPEG$_4$-Biotin, NHS-dPEG$_4$-peptide, glutaric anhydride, fatty acid chloride, and activated ester NHS. Routine experimentation may be used to identify appropriate amidation conditions to prepare polymers that comprise recurring units of the formula II and/or III.

Polymers that comprise a recurring unit of the formula (VII) are another embodiment. Such polymers are useful for, e.g., preparing polymers that comprise a recurring unit of the formula (I). Polymers that comprise a recurring unit of the formula (VII) may be prepared by a process that comprises removing a protecting group from a polymer that comprises a recurring unit of the formula (VIII) via palladium/carbon catalytic hydrogenation:

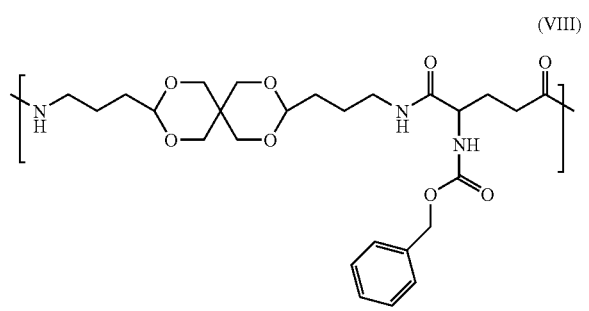

(VIII)

Polymers that comprise a recurring unit of the formula (VII) may also be prepared by a process that comprises treating a polymer that comprises a recurring unit of the formula (IX) with 20% piperidine:

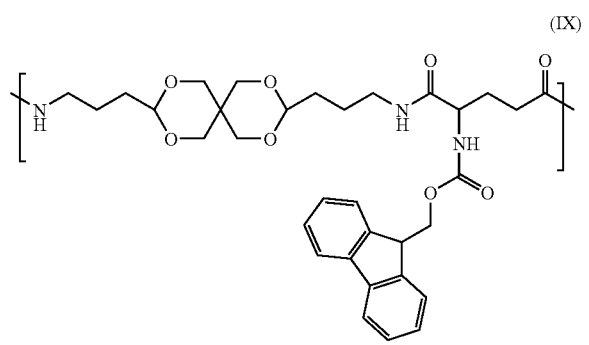

(IX)

Polymers that comprise a recurring unit of the formula (VIII) and polymers that comprise a recurring unit of the formula (IX) are also embodiments. Such polymers are useful for, e.g., preparing polymers that comprise a recurring unit of the formula (VII). Polymers that comprise a recurring unit of the formula (VIII) may be prepared by a process that comprises amidating a diamine and a glutamic amino acid derivative, where the diamine is represented by the formula:

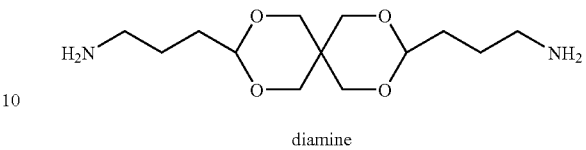

diamine and where the glutamic amino acid derivative is represented by the formula:

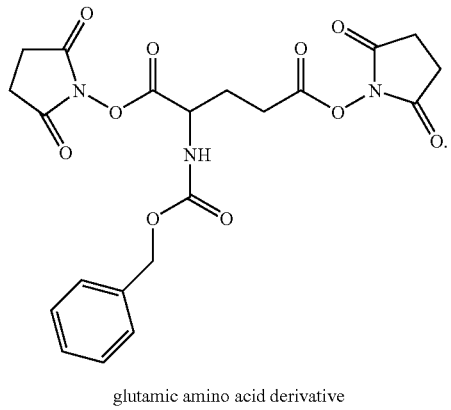

glutamic amino acid derivative

Likewise, polymers that comprise a recurring unit of the formula (IX) may also be prepared by a process that comprises amidating a diamine and a glutamic amino acid derivative, where the diamine is represented by the formula:

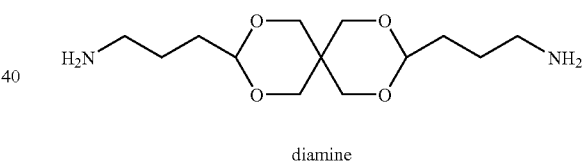

diamine and where the glutamic amino acid derivative is represented by the formula:

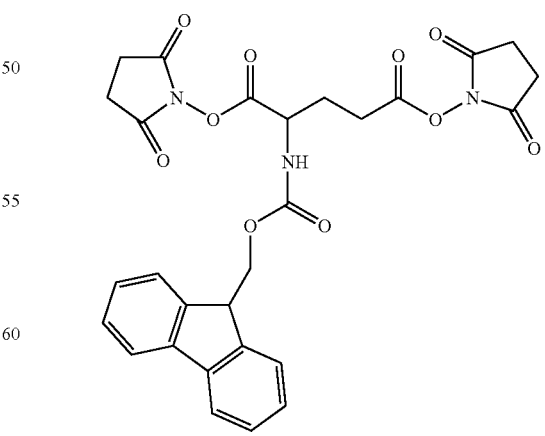

glutamic amino acid derivative

Polymer-Coated Cells and Methods for Making and Using Them

A variety of disease states may be treated according to the embodiments. These include neurologic diseases (e.g. Parkinson's disease, Multiple Sclerosis), cardiovascular disease (myocardial ischemia, repair and regeneration of infarcted myocardium, hepatic (liver failure), diabetes, skin, and renal failure (chronic renal failure, acute renal failure).

The target tissue may be an organ such as heart, brain, kidney, skin, liver, muscle, spleen, lung, spinal cord and bone marrow. The individual being treated is preferably a mammal. The embodiments may be applied in particular to humans and veterinary animals which include but are not limited to horses, sheep, cows, dogs, and cats. Administration may be by injection directly into the organ in need of treatment or by injection into the vascular system feeding the organ in need of treatment.

There are four basic issues for cell-based therapies. These are mobilization of the cells, homing to the target site, integration into the native tissue or organ and survival of the implanted cells. In the context of the invention, the terms "targeting" and "homing" are used interchangeably. The polymer coatings according to the present embodiments are directed particularly to problems relating to integration into native tissue and survival of implanted cells. By coating of the cells with the polymers according to the embodiments, the cells may be protected in the blood for several hours. The polymer coated cells are protected from the immune response of the host. These coatings protect the cell therapeutic while allowing passage of vital nutrients including oxygen. Note that the polymer does not need to completely coat the cell surface in order to provide protection.

The selection of cell type is a function of the disease which is being treated. For example, skeletal myocytes would be injected into post-myocardial infarction scar tissue; neuronal cells would be administered to the brain of patients with Parkinson's Disease. Cell sources which may be used include embryonic stem (ES) cells, adult stem cells, progenitor cells such as skeletal myoblasts, fetal and neonatal cariomyocytes, and chord blood.

The derivation of human ES cells has opened new avenues for using these cells for cellular therapies. ES cells are thought to be a truly pluripotent stem cell capable of self-renewal, can differentiate into all three germ cell layers, and have been shown to form hematopoietic cells and cardiomyocytes. Cells with these properties hold the promise of being able to repair or replace cells or tissues that are damaged or destroyed by many of the most devastating diseases and disabilities. One of the current advantages of using ES cells, as compared to adult stem cells, is that ES cells will proliferate in vitro, and have been used to generate a broad range of cell types through directed differentiation.

Adult stem cells also offer great promise as cell-based therapies and are free of the ethical issues surrounding ES cells. Hematopoietic stem cells give rise to all blood cells and have been used to treat serious blood disorders, malignant disease, and inherited diseases. It has been demonstrated that hematopoietic stem cells can differentiate into cardiac muscle cells, vascular cells, lung epithelium, neural cells, glial cells and other cell lineages. Recently the ability of transplanted or mobilized hematopoietic stem cells to engraft and repair heart muscle and vascular tissue damaged by ischemia has been demonstrated in animal models. In addition, bone marrow derived cells have been demonstrated to engraft as alveolar type 1 epithelial cells and as bronchial epithelial cells.

Cardiovascular and lung tissues may also contain progenitor or stem cells that under the correct conditions could be induced to proliferate and repair cellular damage. For instance, recent findings suggest that a sub-population of fetal proliferative alveolar epithelial stem cells is present in adult lung. In addition, other tissues such as skin, liver, brain, and muscle have progenitor or stem cell populations that may provide additional sources of cells for cellular therapies.

For neovascularization of ischemic myocardium, endothelial progenitor cells may be injected to the target area to promote new vessel growth. The cells are isolated from the mononuclear cell fraction of bone marrow or peripheral blood. The cells may be whole isolated cells or the cells may first be expanded in culture. Other examples include treatment of skin disease with replacement grafts. Skeletal stem cell implantation may be used for bone regeneration. Chondrocytes may be used to repair joint cartilage. Acute and chronic renal failure may be treated with stem/progenitor cells.

The cell source may be either an autologous source or a non-autologous source. In some embodiments, the cells may be genetically modified. In cases where an adequate supply of cells is not possible from the patient due to the disease or other condition, non-autologous sources may be used. Non-autologous cells include allogeneic and xenogeneic cells. Non-autologous sources must overcome the natural host immunologic rejection processes. The polymer coating according to the embodiments provides protection from the host immune response.

The use of autologous cells generally involves obtaining the patient's own cells, expanding the cells in vitro in large quantities over several weeks, and reintroducing the cells in a site-specific manner.

A variety of means for administering cells to individuals in need of treatment will be apparent to those of skill in the art. Such methods include injection of the cells into a target site in a subject. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the embodiments can be introduced into the subject at a desired location. In a preferred embodiment, cells are formulated for administration into a blood vessel via a catheter (where the term "catheter" is intended to include any of the various tube-like systems for delivery of substances to a blood vessel). The cells may be prepared for delivery in a variety of different forms. For example, the cells may be suspended in a solution or gel. Cells may be mixed with a pharmaceutically acceptable carrier or diluent in which the cells of the embodiments remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Modes of administration of the polymer coated cells include but are not limited to systemic intracardiac, intracoronary, intravenous or intra-arterial injection and injection directly into the tissue at the intended site of activity. The preparation can be administered by any convenient route, for example by infusion or bolus injection and can be administered together with other biologically active agents. Administration is preferably systemic. Most preferably, the site of administration is close to or nearest the intended site of activity. In some embodiments, the polymer coated cells will migrate or home to the tissue or organ in need of treatment in response to chemotactic factors produced due to the injury without specific modification of the polymer coated cells for targeting.

Modifications of the polymer coating provide for homing of the cells to the target site. Protein targeting agents such as antibodies or proteins that bind to specific membrane sites may be used to target the polymer coated cells to the target organ or tissue. In some embodiments of the methods described herein, the polymer coated cells are modified prior to implantation into the individual so as to promote their targeting to tissue or organ in need of treatment. For example, the polymer may include an antibody which binds an antigen that is abundant at the target site, that is, at the site of the tissue or organ which is diseased or in need of treatment.

For example, monoclonal antibodies are known that specifically target cancer cells. Many of these are antibodies to growth factor receptors which are preferentially expressed on the surface of cancer cells. These include the humanized monoclonal antibody trastuzumab (Herceptin) which targets the HER-2/neu oncogene (Sato, et al. (2005) Int. J. Radiation Oncology Biol. Phys. vol. 61 (1): 203-211). The HER-2/neu oncogene is found in ovarian cancer, lung cancer, gastric cancer, oral squamous cell carcinoma, breast cancer, and esophageal cancer. BLCA-38 monoclonal antibody has been shown to target prostate and bladder cancer (Russell, et al. (2004) Cancer Immunol Immunother. vol. 53:995-1004). Other monoclonal antibodies are known and it is within the level of skill in the art to select a monoclonal antibody appropriate to the cancer or other disease or injury to be treated.

Migration of polymer coated cells to target tissues may be enhanced by genetic modification, e.g., introduction of an exogenous nucleic acid encoding a homing molecule into the cells. Examples of homing molecules include receptors specific to the target tissue such as chemokine receptors, interleukin receptors, estrogen receptors, and integrin receptors.

In preferred embodiments, a receptor ligand such as transferrin or epidermal growth factor is included in the polymer for homing to cancer cells. These ligands provide specific targeting to receptors on tumor cells. Thus, delivery of the coated cells is localized to the area in need of treatment for maximum effectiveness. Also any adverse effects of the treatment are localized to minimize unwanted side effects.

Another method of homing a cell such as a stem cell to an injured tissue is carried out by increasing the amount of an injury-associated polypeptide, e.g., a cytokine or adhesion protein, in the injured tissue. The method increases the number of stem cells in an area of injured tissue compared to the number of stem cells in the area in the absence of an exogenous injury-associated polypeptide or nucleic acid encoding such a polypeptide. For example, identification of injury-associated polypeptides, e.g., growth factors, activate endogenous mechanisms of repair in the heart such as proliferation and differentiation of cardiac progenitor cells. The injured tissue is contacted with a nucleic acid encoding a protein such as a cytokine or adhesion protein. Alternatively, cells such as fibroblast cells expressing exogenous nucleic acid molecules encoding the cytokine or adhesion protein are introduced to the site of injury.

In one embodiment, the cells optionally contain an exogenous nucleic acid encoding a gene product, which increases endocrine action of the cell, e.g., a gene encoding a hormone, or a paracrine action of the cell. For example, stem cells are genetically modified to contain an exogenous nucleic acid encoding a bone morphogenetic factor and engrafted into bone, cartilage, or tooth tissue, e.g., to treat periodontitis.

The cells optionally also include nucleic acids encoding other biologically active or therapeutic proteins or polypeptides, e.g., angiogenic factors, extracellular matrix proteins, cytokines or growth factors. For example, cells to be engrafted into pancreatic tissue contain a nucleic acid(s) encoding insulin or insulin precursor molecules. The cells also optionally include nucleic acids encoding gene products that decrease transplant rejection, e.g., CTLA4Ig CD40 ligand, or decrease development of transplant arteriosclerosis, e.g., inducible nitric oxide synthase (iNOS).

Tissue specificity is a fundamental problem for gene therapy as proteins that are therapeutic in target cells also may be harmful to normal tissue. Thus non cell-specific expression of a transgene has the potential for inducing metabolic and physiologic mechanisms that could result in pathology over the long term. Localized injections can provide certain degree of localized expression of the targeting vector, however, there may still be a spill over into the circulation which will affect other cells and organs. In some embodiments, transcriptionally targeted vectors may be used that can restrict the expression of the therapeutic proteins primarily to the target cells by the use of tissue-specific promoters.

Once the cells are implanted, maintenance of the cells is dependent upon adequate nutrient and oxygen delivery to the implanted cells. The polymer cell coating according to the embodiments allows for entry of oxygen and other nutrients into the coated cell.

If administration of an immunosuppressant is indicated, one skilled in the art would be able to select a suitable immunosuppressant agent such as cyclosporine, sirolimus, rapamycin, or tacrolimus.

In some embodiments, the polymer includes a label. The label may be a dye or fluorescent label such as Alexa Fluor dyes, BODIPY dyes, Cascade blue dyes, coumarin, Digoxigenin, Environment-Sensitive dyes, Fluorescein, FITC, Haptens, Lissamine Rhodamine B dyes, NBD, Oregon Green dyes, Blue-Fluorescent dyes, photosensitizers, QSY Fluorescent-Dye quenchers, Rhodamine 6G dyes, Rhodamine green dyes, Rhodamine red dyes, tetramethylrhodamine, or Texas red dyes.

Alternatively, the polymer may include a radioactive or a radio-opaque dye such as PET isotopes (18F, 124I, or 76Br) or a radio-opaque dye, e.g., an iodine compound, barium or barium sulfate or gastrografin and the like. After the polymer has bound to the cell, it may then be visualized using well known techniques such as PET, MRI, CT, SPECT, etc (see Molecular Imaging of Gene Expression and Protein Function In Vivo With PET and SPECT, Vijay Sharma, PhD, Gary D. Luker, MD, and David Piwnica-Worms, MD, Ph.D., JOURNAL OF MAGNETIC RESONANCE IMAGING 16:336-351 (2002)).

In preferred embodiments, the polymers described herein may be used advantageously as a coating for cells, particularly cells for use in cell-based therapy applications as described above.

In preferred embodiments, solutions are prepared containing polymers, prepared as described above. Generally, these solutions are prepared at a concentration of 1-50 µg/ml, more preferably about 5-10 µg/ml. The polymer may include any of the modifications described above, including but not limited to cell targeting agents, intracellular-targeting moiety, cytotoxicity reductive reagents, cell binding reagents, cell growing reagents, cell stimulating reagents, cell inhibiting reagents, compounds for culturing specific cells, and/or neutral polymers such as polyethylene glycol co-polymers. In preferred embodiments, a probe is added to the polymer solution.

Cells are seeded in an appropriate vessel such as a multi-well plate, petri dish, or test tube and allowed to grow until 20-70% confluency, preferably 40-60% confluency, most preferably about 50% confluency under conditions appropriate for the cell type used. Any cell type may be coated with the polymers as described herein, including both eukaryotic and prokaryotic cell types. Preferably, the cell is a eukaryotic cell, more preferably the cell type is a mammalian cell. Most preferred cell types include embryonic stem cells, adult stem cells, skeletal myoblasts, fetal and neonatal cariomyocytes and chord blood cells. The cells are checked to insure viability using criteria well known in the art including evaluation of cell morphology and cytotoxic assays. In some preferred embodiments, the buffer/cell culturing solution may be removed and the cells may be washed with a physiologically compatible buffer such as PBS. However, any physiological buffer may be used including but not limited to bicarbonate buffers, monobasic phosphate, 4-(2-hydroxyethyl)-1-piperazineethanesulfonic acid (HEPES), 4-morpholinepropanesulfonic acid (MOPS), 1,4-piperazinebis(ethanesulfonic acid) (PIPES), N-tris(hydroxymethyl)methyl-2-aminoethanesulfonic acid (TES), tris(hydroxymethyl)aminomethane (TRIS BASE), and tris(hydroxymethyl)aminomethane hydrochloride (TRIS.HCl). The polymer solution is then added to the cells on the vessel. The cells are incubated for an appropriate period with the polymer solution to provide a coated cell. Convenient incubation times may be from 5 min. to 2 hours, preferably 10 min. to 30 min., most preferably about 15 min. The cells may optionally be washed with physiological buffer as described above.

Alternatively, cells may be harvested by centrifugation. The cells are preferably dividing cells. The harvested cells may optionally be washed in an appropriate buffer as described above. The washing buffer is then removed by centrifugation. The cells are then suspended in the polymer solution and incubated as described above. The polymer solution may be removed by centrifugation. The cells are then optionally washed again with a physiological buffer as described above to remove residual polymer.

EXAMPLES

All starting materials, solvents, and reagents were purchased from commercial sources and used without further purification. Molecular weights are weight average and were determined by aqueous gel permeation chromatography (GPC) using polyethlyene glycol standards. Chemical structures were confirmed by $^1$H and $^{13}$C NMR spectra measured at room temperature on a 400 MHz (100 MHz for $^{13}$C) instrument in $D_2O$ or DMSO-$d_6$.

Examples 1-3

A polymer 4 comprising a recurring unit of the formula (VIII) is prepared by amidating a diamine and a glutamic amino acid derivative according to the reaction scheme illustrated in FIG. 1 as follows: A solution of glutamic amino acid derivative 2 (1.5 g, 3.2 mmol) in acetone (25 mL) is added into a solution of diamine 1 (0.87 g, 3.2 mmol) in acetone (10 mL) at room temperature with stirring. White precipitate forms after a few minutes. Stirring is continued for about 15 minutes. The solution is decanted and the residue is washed with additional acetone. The resulting polymer 4 (0.87 g, 1.67 mmol) is obtained after drying the residue under high vacuum. The weight average molecular weight of the polymer 4 is about 45,000 daltons with a polydispersity of about 1.48. Similar reactions carried out in dichloromethane (DCM) and dimethylformamide (DMF) also produce polymer 4, in these cases having weight average molecular weights of about 45,000 daltons (PDI 1.42) and about 58,000 daltons (PDI 1.37), respectively.

Example 4

A polymer 5 comprising a recurring unit of the formula (IX) is prepared by amidating a diamine and a glutamic amino acid derivative according to the reaction scheme illustrated in FIG. 1 in a manner similar to that described in Examples 1-3 using acetone as a solvent, except that glutamic amino acid derivative 3 is used in place of 2 as illustrated in FIG. 1. The weight average molecular weight of the resulting polymer 5 is about 10,000-12,000 daltons.

Example 5

A polymer 6 that comprises a recurring unit of the formula (VII) is prepared by a process that comprises removing a CBZ protecting group from the polymer 4 (prepared as described in Examples 1-3) that comprises a recurring unit of the formula (VIII) via palladium/carbon catalytic hydrogenation according to the scheme illustrated in FIG. 1 as follows: CAUTION!! Pd/C is highly flammable when flammable solvents are near. This procedure should be conducted under an argon or nitrogen atmosphere. A sample of the polymer 4 (4.0 g) is added into a 500-mL flask equipped with a stirring bar. Pd/C (10%, 0.5 g) is added into the flask. The flask is purged with argon. Deoxygenated methanol (150 mL) is added into the flask. Hydrogen gas (1 atm) is introduced and the mixture is stirred under 1 atm hydrogen gas for 1 day. The insoluble residue is filtered. The filtrate is concentrated by rotary evaporation to provide a residue. The resulting polymer 6 (3.0 g) is obtained after drying the residue under high vacuum.

Example 6

Figure 2:
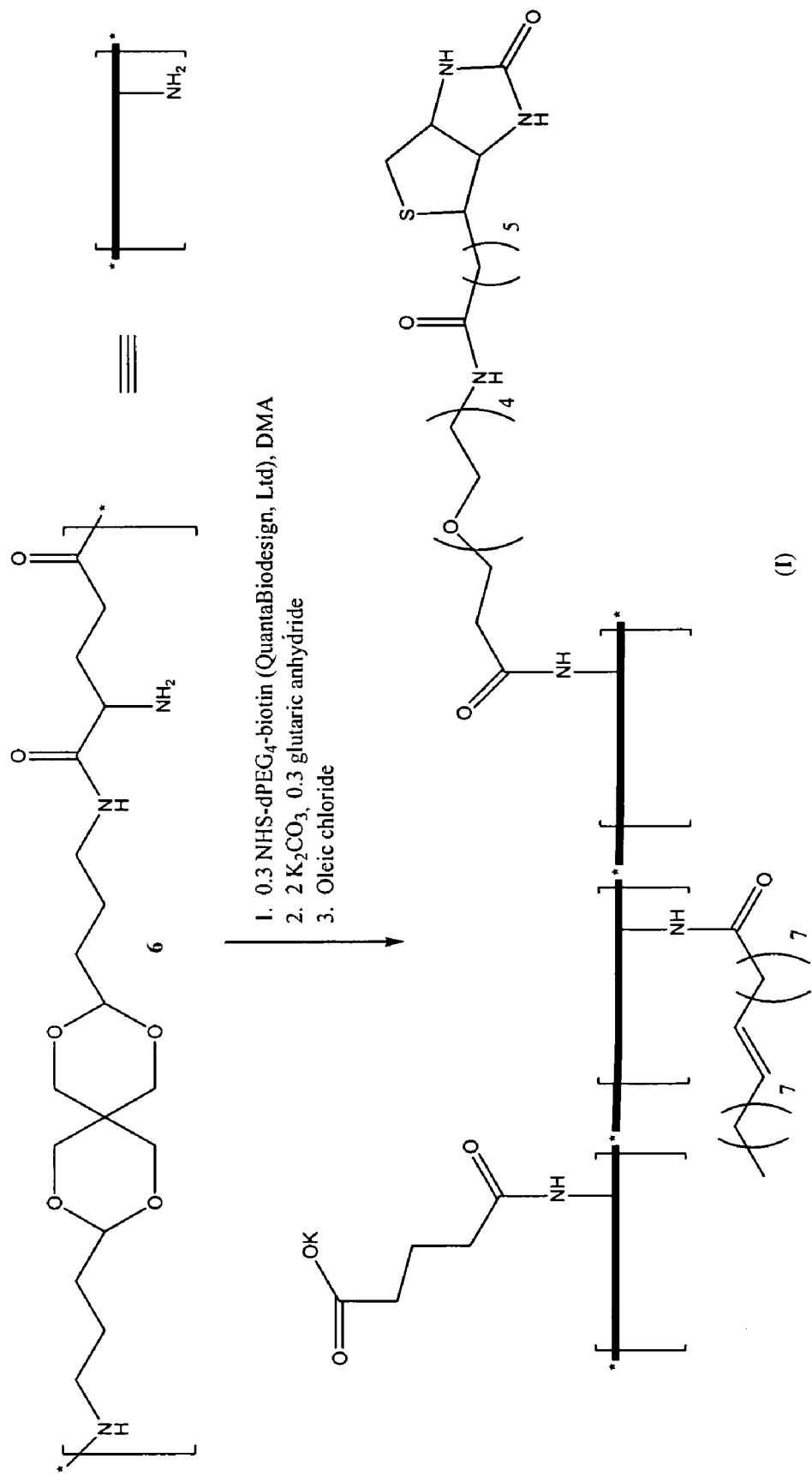
FIG. 2 shows a reaction scheme according to an embodiment for preparation of polymers by amidation of the polymer 6 with NHS-dPEG$_4$-Biotin, glutaric anhydride, and oleic chloride.

A polymer that comprises a recurring unit of the formula (I) (specifically, a polymer that comprises recurring units of the formulas (IV), (V) and (VI)) is prepared by a process that comprises amidating the polymer 6 (comprising a recurring unit of the formula (VII)) with NHS-dPEG$_4$-Biotin, glutaric anhydride, and oleic chloride according to the scheme illustrated in FIG. 2 as follows: A sample of the polymer 6 (105 mg) is dissolved in dimethylacetamide (DMA) (3 mL). Anhydrous potassium carbonate (100 mg) is added into the mixture. NHS-dPEG$_4$-biotin (QuantaBiodesign, Ltd) (50 mg) is added into the mixture and stirred for about 20 min. Glutaric anhydride (10 mg) is added and stirring is continued for about 2 hours. Oleic chloride (95 μL) is added and stirring is continued for about 5 min. The reaction is quenched with water (5 mL) and acetone (5 mL) is added to induce precipitation. The residue is centrifuged and isolated. The residue is purified by sephadex-G25 gel filtration, and the product polymer IA comprising a recurring unit of the formula (I) is obtained in fractions after freeze-drying.

Example 7

Figure 3:
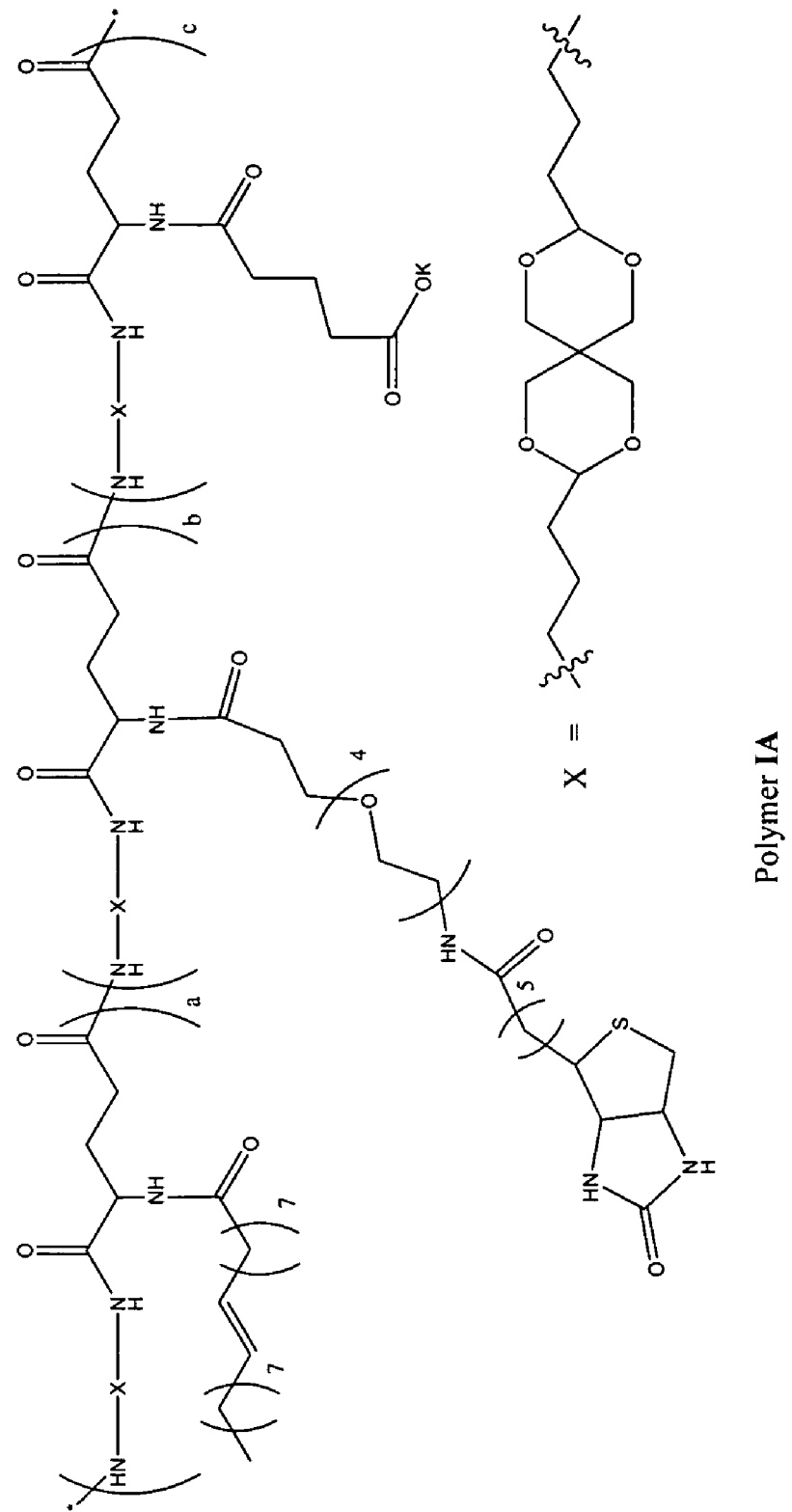
FIG. 3 shows the polymer IA produced by the reaction scheme of FIG. 2 as described in Example 6.

A sample of polymer IA (prepared as in Example 6 above) was used in this example (see FIG. 3, polymer IA). The polymer was prepared at two different concentrations of 10 μg/mL and 5 μg/mL in PBS. Streptavidin-Alexa 448 (Molecular Probes, Inc.) was diluted in 25 μg/mL in PBS. The streptavidin-green fluorescene Alexa was added to the cells to monitor binding of the polymer to the cells. When Streptavidin binds to the biotin moiety on the polymer, a green fluorescence is observed.

Lung cancer cells (A549 cells) were seeded in 6-well plates overnight with approximately 50% confluency. Cell morphology was checked to insure no detachment from the plates. Buffers were removed from the cells and the cells were washed twice with 2 mL PBS. PBS was used as the negative control in one well. The other wells received 1 mL of the polymer IA of FIG. 3 per well. The cells were incubated with the polymer solutions for 15 min. The solution containing the polymer was removed. The cells were washed again twice with PBS, 2 mL. Streptavidin-Alexa 488 solution was added (1 mL). The coated cells and negative control were incubated with the streptavidin solution for 30 min. Convenient incubation times may be from 2 min. to 1 hour. The solution containing the streptavidin was removed from the cells. The cells were washed again twice in 2 mL of PBS. PBS (500 μL) was added and the cells were viewed in a fluorescence microscope. The results are shown in FIG. 4.

Figure 4:
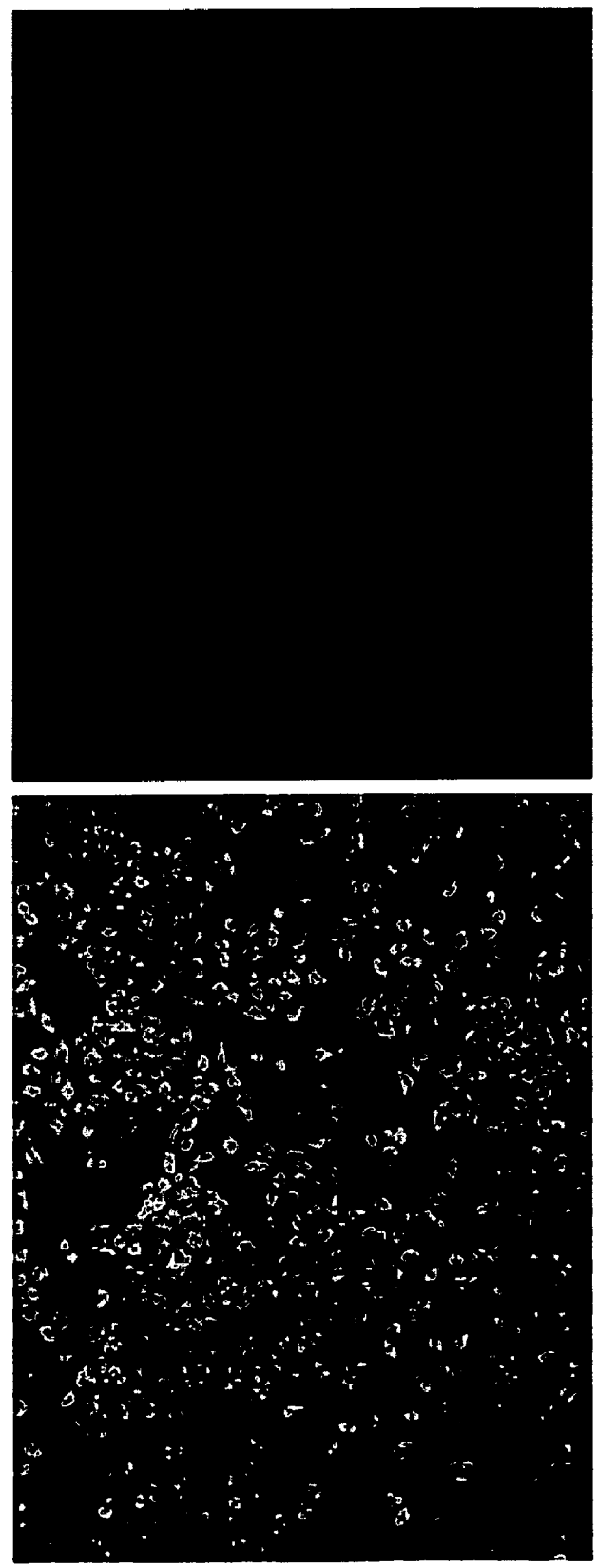
FIG. 4 shows lung cancer cells in the presence (left side) and absence (right side) of Polymer IA. Both treatments were treated with Streptavidin-Alexa 448 to visualize the binding.

FIG. 4 shows that the cells treated with polymer IA as described above are strongly fluorescent due to the binding of the streptavidin-fluorescene to the biotin moiety on the polymer. In contrast, the control treatment shown on the right shows no fluorescence. Even though the fluorescent binding agent was added to the control cells, there was no binding in the absence of the polymer. This experiment demonstrates successful polymer coating of the cell.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A polymer comprising at least one recurring unit represented by formula (I):

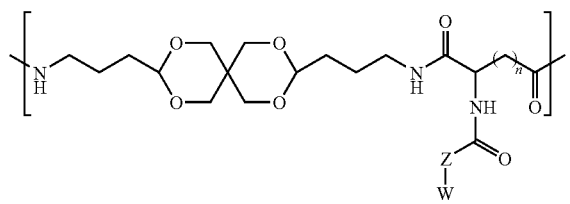

(I)

wherein n is 1 or 2; wherein Z is an optional linker group comprising from about zero to about 20 carbon atoms, from about zero to about 5 oxygen atoms, from about zero to about five nitrogen atoms, from about zero to about 5 sulfur atoms, and from about zero to about five phosphorous atoms; and wherein each W is individually selected from the group consisting of biotin, a fatty acid, a fluorescent dye, an antibody, a peptide, a targeting ligand, a polysaccharide, a carboxybenzyl group (CBZ), and a negatively charged group.

2. The polymer of claim 1 in which the fatty acid comprises a moiety selected from the group consisting of oleic, stearyl, palmitic, linoleic, linolenoic, and cholesteryl.

3. The polymer of claim 1 in which the negatively charged group is selected from the group consisting of $C(=O)O^-$, $SO_3^-$, and $PO_4^{2-}$.

4. The polymer of claim 1 comprising at least one recurring unit selected from the group consisting of a recurring unit of the formula (IV), a recurring unit of the formula (V), and a recurring unit of the formula (VI):

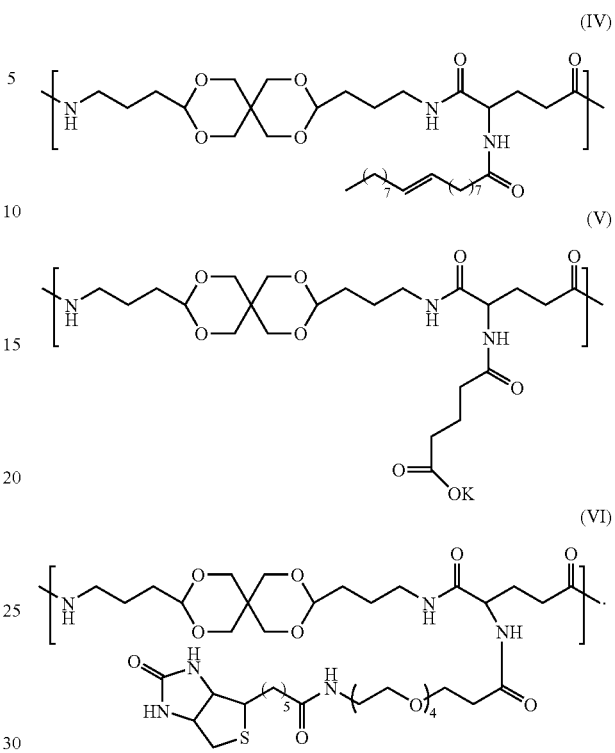

5. The polymer of claim 4 comprising a recurring unit of the formula (IV), a recurring unit of the formula (V), and a recurring unit of the formula (VI).

6. The polymer of claim 1 comprising a recurring unit of the formula (VIII):

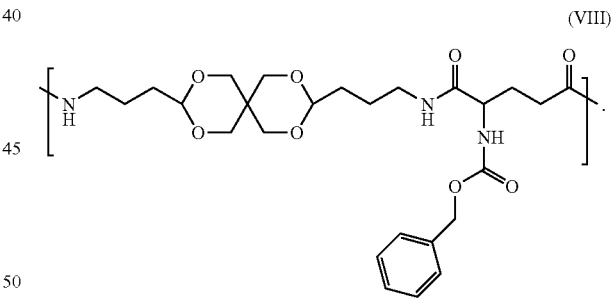

7. A method of making the polymer of claim 1 that comprises a recurring unit of the formula (I)

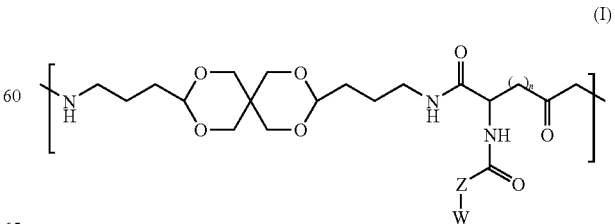

(I)

comprising amidating a polymer that comprises a recurring unit of the formula (VII)

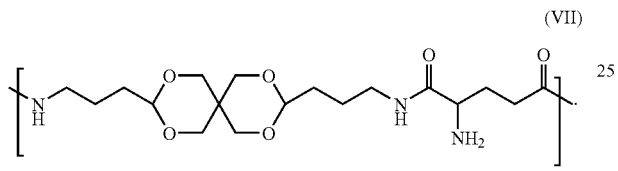
(VII)

with a reagent selected from the group consisting of NHS-dPEG$_4$-Biotin, NHS-dPEG$_4$-peptide, glutaric anhydride, fatty acid chloride, and activated ester NHS.

8. A method of making the polymer of claim 4 that comprises a recurring unit of the formula (IV), comprising amidating a polymer that comprises a recurring unit of the formula (VII) with oleic chloride.

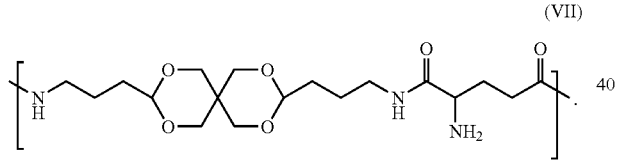
(VII)

9. A method of making the polymer of claim 4 that comprises a recurring unit of the formula (V), comprising amidating a polymer that comprises a recurring unit of the formula (VII) with glutaric anhydride and potassium carbonate (VII)

10. A method of making the polymer of claim 4 that comprises a recurring unit of the formula (VI), comprising amidating a polymer that comprises a recurring unit of the formula (VII) with NHS-dPEG$_4$-Biotin

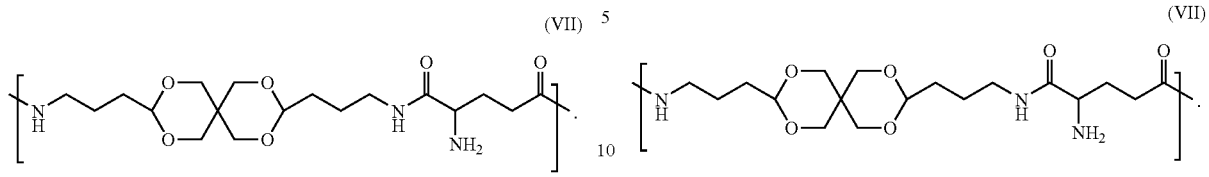
(VII)

11. A method of making the polymer of claim 6, comprising amidating a diamine and a glutamic amino acid derivative, wherein the diamine is represented by the formula:

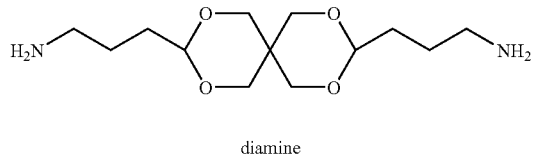

diamine and wherein the glutamic amino acid derivative is represented by the formula:

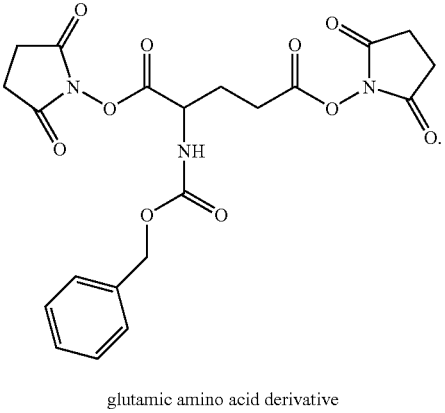

glutamic amino acid derivative

\* \* \* \* \*

UNITED STATES PATENT AND TRADEMARK OFFICE
CERTIFICATE OF CORRECTION

PATENT NO. : 7,674,452 B2
APPLICATION NO. : 11/359811
DATED : March 9, 2010
INVENTOR(S) : Van et al.

It is certified that error appears in the above-identified patent and that said Letters Patent is hereby corrected as shown below:

Title Page 1, Column 2 (Item 56), Line 53, Under Other Publications, change "Lancer," to --Langer,--.

Title Page 2, Column 2 (Item 56), Line 6, Under Other Publications, change "Lancer," to --Langer,--.

At Column 7, Line 62 (Approx.), change "or PO42-" to --and PO42- --.

At Column 11, Line 39, change "cariomyocytes," to --cardiomyocytes,--.

At Column 11, Line 40, change "chord" to --cord--.

At Column 15, Line 5, change "cariomyocytes" to --cardiomyocytes--.

At Column 15, Line 6, change "chord" to --cord--.

At Column 15, Line 44, change "polyethlyene" to --polyethylene--.

At Column 16, Line 64, change "fluorescene" to --fluorescein--.

At Column 17, Line 20, change "streptavidin-fluorescene" to --streptavidin-fluorescein--.

At Column 18, Line 60, in Claim 7, change

"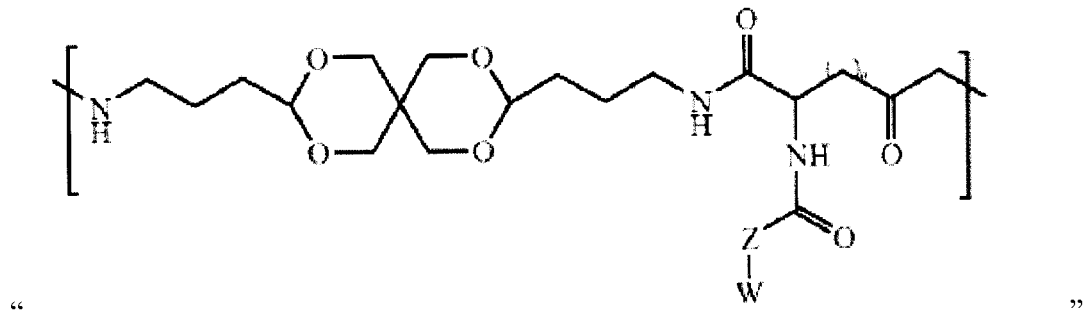"

Signed and Sealed this

Ninth Day of November, 2010

David J. Kappos
*Director of the United States Patent and Trademark Office*

CERTIFICATE OF CORRECTION (continued)
U.S. Pat. No. 7,674,452 B2 to

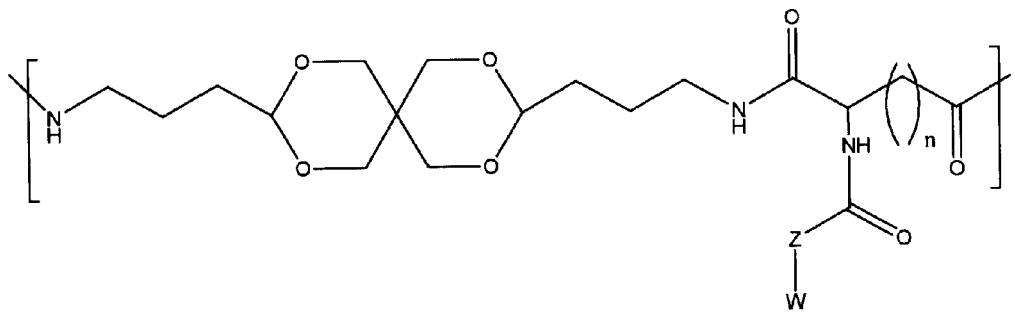

--                                                                --.